(12) United States Patent
Dupuis et al.

(10) Patent No.: US 6,338,858 B1
(45) Date of Patent: Jan. 15, 2002

(54) TOPICAL AQUEOUS GEL COMPOSITION

(75) Inventors: Christine Dupuis, Paris; Henri Samain, Bievres; Véronique Roulier, Paris; Véronique Ferrari, Maisons-Alfort, all of (FR)

(73) Assignee: L'Oreal (FR)

( * ) Notice: Subject to any disclaimer, the term of this patent is extended or adjusted under 35 U.S.C. 154(b) by 0 days.

(21) Appl. No.: 09/039,399

(22) Filed: Mar. 16, 1998

(30) Foreign Application Priority Data

Mar. 14, 1997 (FR) ............................................ 97 03119

(51) Int. Cl.[7] .......................... A61K 9/10; A61K 7/027; A61K 7/11; A61K 7/32; A61K 47/34
(52) U.S. Cl. ...................... 424/486; 424/70.11; 424/64; 424/65; 424/DIG. 2; 424/DIG. 4; 424/DIG. 5
(58) Field of Search .................................. 424/401, 486, 424/63–64, 70.11, 78.02, 78.03, 78.05–78.07, 65, DIG. 2, DIG. 4–5; 514/844, 852, 772.1, 880–881; 510/158

(56) References Cited

U.S. PATENT DOCUMENTS

| | | | |
|---|---|---|---|
| 3,779,993 A | * | 12/1973 | Kibler et al. |
| 4,300,580 A | | 11/1981 | O'Neill et al. ................. 132/7 |
| 4,525,524 A | | 6/1985 | Tung et al. ................. 524/601 |
| 5,639,448 A | * | 6/1997 | Galleguillos et al. |
| 5,849,280 A | * | 12/1998 | Rechelbacher et al. |

FOREIGN PATENT DOCUMENTS

| | | |
|---|---|---|
| WO | WO 96/03964 | 2/1996 |

OTHER PUBLICATIONS

Minako Juchi et al., "Cosmetics Containing Polyester Particles", Chemical Abstracts, vol. 120, No. 14, Apr. 4, 1994.

* cited by examiner

Primary Examiner—Edward J. Webman
(74) Attorney, Agent, or Firm—Finnegan, Henderson, Farabow, Garrett & Dunner

(57) ABSTRACT

An aqueous solid topical composition comprising a matrix, i.e., an aqueous solid matrix, having the appearance of a gel and possessing the following rheological profile:

an initial viscosity at rest $V_0$ sufficient to form a solid composition, preferably ranging from 50,000 to 1,000,000 Pa·s, said viscosity $V_0$ being stable up to a shear strain $C_1$, a viscosity $V_2$ after shear at a strain $C_2$ for which the ratio $V_0/V_2$ is greater than or equal to 1000:1, the difference $C_2-C_1$ being less than or equal to 1000 Pa, and which may be useful as a make-up, styling, body hygiene or care composition.

24 Claims, No Drawings

TOPICAL AQUEOUS GEL COMPOSITION

The present invention relates to a novel solid aqueous composition, in particular a topical composition, consisting of a matrix having the appearance of an aqueous gel, this composition allowing a film to be formed when it is applied.

Various types of products in the form of a solid are known in the cosmetics industry, in particular in the field of make-up, such as lip compositions, foundations or eye shadows, in the field of skin or lip care, such as lip-repairing pencils and depigmenting or moisturizing sticks, and in the hygiene field, such as deodorant sticks. The composition is applied by abrasion, which makes it difficult to form durable, continuous films.

This problem of forming continuous films by applying a solid composition is particularly important for make-up compositions which are composed of a heterogeneous mixture of waxes, oils and powders (fillers and pigments), more particularly for so-called "transfer-free" make-up compositions, i.e. compositions whose constituents do not transfer onto supports with which they may come into contact (for example fabrics, glasses, cups, etc.). The reason for this is that making a "transfer-free" make-up composition requires the use of a complex composition in which the oils are partially replaced by volatile solvents which evaporate on contact with the skin, to leave a layer composed essentially of waxes and/or resins and pigments and fillers (See JP 62-61911, JP 61-65809, and EP 602,905). Apart from the preparation difficulties associated with the use of volatile compounds, this solution has the drawback of leading to a make-up effect of powdery and matte appearance.

The inventors have now found that by using a solid matrix having the appearance of an aqueous gel and possessing a specific rheological profile, it is possible to obtain a solid aqueous composition which allows the formation of a film after its application and drying, thus providing a solution to the problems outlined above.

A subject of the present invention is thus an aqueous solid topical composition consisting of a solid matrix having the appearance of an aqueous gel and possessing the following rheological profile:

an initial viscosity at rest $V_0$ which is sufficient to form a solid composition, preferably ranging from 50,000 to 1,000,000 Pa·s, the viscosity $V_0$ being stable up to a shear strain cl, a viscosity $V_2$ after shear at a strain $C_2$ for which the ratio $V_0/V_2$ is greater than or equal to 1000, the difference $C_2-C_1$ being less than or equal to 1000 Pa.

The solid matrix has an initial viscosity which is stable, i.e. constant under low shear strains, such that the composition can be manipulated without this leading to a large change in its viscosity. This stability of the initial viscosity is expressed by a value of the viscosity of the gel $V_1$ measured at the shear strain $C_1$ close to $V_0$. It is understood that this proximity should be assessed with regard to the fall in viscosity after shear. Advantageously, the ratio $V_0/V_1$ is less than or equal to 2.

The shear strain $C_1$ is characteristic of the force required to fluidize the solid matrix, allowing it to spread on the support on which it is applied, skin, hair, lips, etc. Preferably, the shear strain $C_1$ is greater than or equal to 500 Pa. However, a person skilled in the art will know how to determine the value which this shear strain $C_1$ must not exceed in order not to adversely affect this support.

Thus, for application to the hair, the starting shear strain $C_1$ is advantageously less than or equal to 1500 Pa.

It is understood hereinabove and hereinbelow that the various viscosity and strain values are measured once the matrix has been formed. Before measuring the viscosity and rheological profile of the composition, it is worthwhile ensuring that the matrix has formed correctly and is stable. It is thus worth waiting at least 24 hours after the matrix has been prepared.

Preferably, the falls in viscosity induced by shear on the composition are not immediately reversible, i.e. the matrix does not break under high strain and remains homogeneous when it has reached its lowest viscosity.

Advantageously, this matrix is formed by adding a suitable hydrophilic gelling material.

The hydrophilic gelling material according to the invention comprises any gelling material capable of forming a solid matrix having the appearance of a gel and possessing the rheological profile according to the invention.

According to a preferred embodiment of the invention, the hydrophilic gelling material is a hydrophilic gelling polymer. Hydrophilic gelling polymers that are useful according to the invention are, in particular, polyester sulphones preferably with a weight-average molecular mass of less than 20,000, more preferably less than 15,000.

Such polymers can be, more particularly, water-soluble or water-dispersible terephthalic copolyester oligomers essentially comprising repeating dicarboxylate units of formula (I):

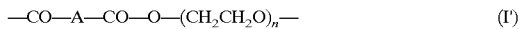

$$—CO—A—CO—O—(CH_2CH_2O)_n— \qquad (I')$$

in which

A represents a 1,4-phenylene, sulpho-1,3-phenylene or 1,3-phenylene group, n ranges from 1 to 4, wherein at least 35 mol % of the units of formula (I) are units of formula (I) for which A represents a 1,4-phenylene group and n is equal to 1, at least 7 mol % of the units of formula (I) are units of formula (I) for which A represents a sulpho-1,3-phenylene group, and the weight-average molecular mass of the copolyester oligomers is preferably less than 20,000, more preferably less than 15,000.

Preferably, at least 40 mol %, more preferably from 40 to 90 mol %, of the units of formula (I) are units of formula (I) for which A represents a 1,4-phenylene group and n is equal to 1.

Preferably, at least 10 mol %, more preferably from 10 mol % to 25 mol %, of the units of formula (I) are units of formula (I) for which A represents a sulpho-1,3-phenylene group.

The ends of the chains of the copolyester oligomers can be similar or different and can be represented by groups of formula (I'):

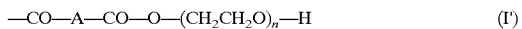

$$—CO—A—CO—O—(CH_2CH_2O)_n—H \qquad (I')$$

in which A and n are defined above.

The oligomers can also have at the chain ends, and in smaller amounts, groups of formulae

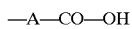

—A—CO—OH

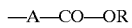

—A—CO—OR in which formulae A is defined above and R represents a $C_1$–$C_4$ alkyl group.

When A represents a sulpho-1,3-phenylene group, it is more particularly an alkali metal sulphonate, in particular sodium or potassium sulphonate, or an ammonium or lower mono-, di-, tri- or tetraalkylammonium sulphonate. According to the invention, the term lower alkylammonium is preferably understood to refer to an ammonium in which the alkyl radical(s) is(are) lower alkyls, preferably $C_1$–$C_6$ alkyls. Preferably, A is a sodium sulphonate.

The copolyester oligomer can optionally comprise up to 20 mol %, more preferably up to 5 mol %, of units of formula (I) for which A represents a 1,3-phenylene group.

According to a preferred embodiment of the invention, the above copolyester oligomer has a weight-average molecular mass ranging from 5000 to 14,000, more preferably from 8000 to 10,000.

The weight-average molecular masses are measured by gel permeation chromatography in dimethylacetamide containing $10^{-2}$ N of LiBr, at 100° C. The results are expressed in polystyrene equivalents.

The copolyester oligomers can be obtained by the usual molten-route, solvent-route or interface-route processes for preparing polyesters, these processes involving
- esterification reactions of diacids and of diols and polycondensation
- transesterification reactions of diesters and of diols and polycondensation
- autocondensation reactions of hydroxy acids
- Schoften-Baumann reactions using diols and acid chlorides, and polycondensation
- polymerization reactions of lactones while controlling the minimum content of units of formula (I) for which A represents a 1,4-phenylene group and n is equal to 1, which are similar on the basis of the initial stoichiometric ratios of the various monomers and on the basis of the control of the side reactions.

A particularly advantageous mode of preparation is that by molten-route transesterification/polycondensation and/or esterification/polycondensation using a transesterification and/or esterification catalyst.

The control of the structure is obtained by controlling the minimum content of units of formula (I) for which A represents a 1,4-phenylene group and n is equal to 1, which are similar on the basis of the initial stoichiometric ratios of the various diacid and/or diester and diol monomers and on the basis of the use of an etherification-limiting agent, it being possible for this limiting agent to be a basic compound such as aliphatic or aromatic amines, or an alkali-metal or alkaline-earth metal hydroxide or acetate.

The control of the molecular mass is obtained in a manner which is known per se to those skilled in the art, by achieving a suitable compromise between pressure, temperature and time.

The novel terephthalic copolyester oligomers which form the subject of the invention can be prepared by esterification and/or transesterification/polycondensation of a monomer composition based:
- on terephthalic (Tp) acid, anhydride or diester
- on sulphoisophthalic (SIp) acid, anhydride or diester
- optionally on isophthalic (Ip) acid, anhydride or diester, and
- on ethylene glycol (EG)

in relative amounts corresponding to
- an (SIp)/[(Tp)+(SIp)+(Ip)] molar ratio preferably of at least 7/100, more preferably of at least 10/100, and even more preferably from 10/100 to 25/100
- an (Ip)/[(Tp)+(SIp)+(Ip)] molar ratio preferably of not more than 20/100, more preferably of not more than 5/100
- an (EG)/[(Tp)+(SIp)+(Ip)] molar ratio preferably of from 2/1 to 3/1 in the presence of an esterification and/or transesterification catalyst and an etherification-limiting agent.

The terephthalic (Tp) monomer is preferably used in the form of a lower diester (di($C_1$–$C_4$)alkyl diester), more preferably the dimethyl diester.

The sulphoisophthalic (SIp) monomer is preferably used in the form of an alkali metal sulphonate (in particular sodium sulphonate) of a lower ($C_1$–$C_4$ alkyl), preferably methyl, diester. Sodium dimethyl 5-oxysulphonylisophthalate may be mentioned most particularly.

The optional isophthalic (Ip) monomer is preferably used in the form of isophthalic acid.

When all of the "diacid" monomers are used in the form of diesters, the transesterification (exchange) operation between these "diacid" monomers and ethylene glycol is preferably carried out at a temperature above or equal to 130° C., more preferably of about 140 to 220° C. and even more preferably of about 180 to 220° C.; at this temperature the methanol (in the preferred case of the dimethyl diesters) formed is preferably removed from the reaction medium by distillation.

This exchange operation is carried out in the presence of a metallic transesterification catalyst and an etherification-limiting agent. The catalyst is preferably a metal carboxylate, such as manganese acetate, zinc acetate, cobalt acetate or calcium acetate, or an organic or inorganic titanate such as butyl titanate, nitrilo-2,2',2"-triethyl titanate (or titanium aminotriethanolate which also acts as etherification-limiting agent) or calcium titanate. The preferred catalysts are the organic titanates; they are used in amounts preferably of at least about 0.001% by weight, expressed as titanium, more preferably from about 0.002% to 0.02% by weight of titanium relative to the weight of reactants present.

The etherification-limiting agent can be a basic compound such as aliphatic or aromatic amines (triethanolamine, guanidine carbonate, dimethylaniline, naphthylamine, etc.) or an alkali-metal or alkaline-earth metal hydroxide or acetate (sodium or potassium acetate, sodium benzoate, etc.). It is generally used in an amount ranging from about 0.001% to 0.05% relative to the weight of reactants present.

The duration of the exchange operation is preferably from 1 to 4 hours; more preferably from about 2 to 3 hours.

When more than 90% of the theoretical amount of methanol has been distilled off, the excess polyol is removed by bringing the temperature of the reaction medium to 230° C.

The polycondensation operation is preferably carried out at a temperature ranging from about 230 to 280° C., more preferably from about 240 to 260° C., in another reactor brought beforehand to this temperature and gradually placed under vacuum down to a pressure which may be as low as 10 Pa; a pressure reduction down to about 10 millibar lasts for about 40 minutes.

The polycondensation operation takes place with removal of polyol molecules, this operation being stopped when the motor torque of the stirrer shaft indicates a value equivalent to about 0.5 to 5 newton.metres for a temperature of 250° C. of the reaction mass and a stirring speed of 80 revolutions/minute of an anchor-shaped spindle in a 7.5-liter reactor. The vacuum is then broken with nitrogen and the polymer is poured into a mould; after cooling, the polymer is ground.

When one of the "diacid" monomers is present in the form of diacid or anhydride and the other(s) is(are) in the form of diester(s), the copolyester oligomers are obtained by first carrying out a transesterification operation of the diester monomers with ethylene glycol under the conditions described above, followed by an esterification operation in the medium of the diacid or anhydride monomer with ethylene glycol, and then polycondensation under the conditions described above, the total amount of ethylene glycol being divided between the two operations (transesterification and esterification).

If necessary, the esterification operation is carried out by adding, to the reaction medium resulting from the transesterification operation, the monomer in diacid or anhydride form and ethylene glycol placed in suspension beforehand, at a temperature corresponding to that at the end of the exchange; the introduction period is about 1 hour.

This esterification operation is preferably carried out at a temperature ranging from about 230 to 280° C., more preferably from about 250 to 260° C., in the presence of a catalyst of the same type as the transesterification catalyst, and an etherification-limiting agent.

The operation is carried out in the presence of the same types of catalyst and of etherification-limiting agent as those used in the transesterification operation, and in the same proportions.

The reaction is carried out with removal of water, which is removed from the reactor at the same time as the excess polyol.

This type of preparation process is described in particular in patent application WO 95/32997 (Rhone-Poulenc Chimie), the disclosure of which is specifically incorporated by reference herein.

Preferably, the composition according to the invention comprises from 10 to 40% by weight of hydrophilic gelling material relative to the total weight of the composition, more preferably from 10 to 30% by weight.

The topical composition according to the invention is preferably a cosmetic or pharmaceutical composition intended to be applied to the skin, mucous membranes or the exoskeleton (hair, eyelashes, nails, etc.).

The composition can be used for any common dermocosmetic use, and in particular as a body hygiene composition, for example in the form of deodorant sticks, as a hair composition, for example as a styling stick, as a make-up composition like a lip composition, a foundation, an eye shadow, etc., in particular as a so-called "transfer-free" make-up composition, or alternatively as a care composition.

The composition according to the invention can thus comprise other constituents that are common in cosmetics depending on the use which is envisaged. Obviously, the composition according to the invention will not comprise any constituents in amounts liable to adversely affect the specific rheological properties of the solid matrix constituting it.

The composition according to the invention can also comprise a fatty phase. The fatty phase can comprise oils or waxes that are common in cosmetics, of animal, plant, mineral or synthetic origin, alone or as mixtures. In this case, the fatty phase can be dispersed in the gel, in particular in the form of an emulsion of oil-in-water or water-in-oil type.

The composition according to the invention can comprise additives and/or active agents that are common in dermocosmetics, it being understood that a person skilled in the art will know how to determine the amounts of these additives and active agents which may be added to the composition according to the invention so as not to adversely affect the rheological profile of the solid matrix constituting it.

The common cosmetic additives are, in particular, fragrances, dyes, odor absorbers, additives for stabilizing the composition, such as preserving agents, UVA and/or UVB screening agents, hydrophilic and/or lipophilic antioxidants, chelating agents, etc. The amounts of these various adjuvants are those used conventionally in the field considered, and, for example, from 0.0001 to 5% by weight relative to the total weight of the composition. Depending on their nature, these adjuvants can be introduced into the aqueous phase or into the fatty phase when the composition also comprises a fatty phase.

The composition according to the invention can also comprise hydrophilic and/or lipophilic active agents that are common in cosmetics, in particular anti-free-radical agents, α- or β-hydroxy acids, UVA and/or UVB screening agents, ceramides, antidandruff agents such as octopirox or zinc pyrithione, antiacne agents such as retinoic acid or benzoyl peroxide, agents for combating hair loss such as minoxidil, antifungal or antiseptic agents, etc.

For use as a body hygiene composition, the composition according to the invention can comprise deodorant products containing active substances of antiperspirant type and/or of bactericidal type in order to reduce or even eliminate the generally unpleasant underarm odors, and/or odour absorbers.

The antiperspirant substances have the effect of limiting the flow of sweat. They consist in particular of aluminium salts.

The bactericidal substances inhibit the growth of the skin flora responsible for underarm odours. Among these bactericidal products, mention may be made of triclosan (5-chloro-2-(2,4-dichlorophenoxy)phenol).

The odour absorbers are products which are capable of taking up and retaining inside them the molecules responsible for unpleasant odours (this definition is given in the book "Cosmetic Science and Technology Series"—1988/Volume 7, Chap. 10—IIIc, the disclosure of which is specifically incorporated by reference herein). These products have the effect of reducing to a greater or lesser extent the odour of sweat which has already developed. Among the odour absorbers, mention may be made of zinc salts, in particular the zinc salts of polycarboxylic acids described in U.S. Pat. No. 4,425,321, the disclosure of which is specifically incorporated by reference herein, and in particular those of dimerginic acid and those of hydroxylated or unhydroxylated trimerginic acid. Mention may also be made of water-soluble zinc salts.

For use as a hair composition, owing to the specific rheological properties of the solid matrix constituting it, the composition according to the invention affords a good styling effect and discipline to the hair style.

In order to obtain a fixing effect or to improve the styling and disentangling effect, a fixing material or a conditioning material can be added to the composition according to the invention. These fixing or conditioning materials can preferably be used in amounts ranging from 0.01 to 15% by weight relative to the total weight of the composition, more preferably from 0.1 to 8% by weight.

The composition according to the invention can also comprise hair care active agents and/or sheen reinforcers and/or hair dyes. These active agents and/or hair agents can be used in amounts preferably ranging from 0.01 to 20% by weight relative to the total weight of the composition according to the invention.

The fixing materials which are useful according to the invention comprise at least one fixing polymer, alone or in combination with common cosmetic additives, such as plasticizers, or neutralizing agents. According to the invention, any fixing polymer known per se can be used. In particular, a fixing polymer chosen from anionic, cationic, amphoteric and nonionic polymers and mixtures thereof can be used. The anionic or amphoteric fixing polymers can, if necessary, be partially or totally neutralized. The neutralizing agents are, for example, sodium hydroxide, potassium hydroxide, 2-amino-2-methyl-1-propanol, monoethanolamine, triethanolamine or triisopropanolamine, and inorganic or organic acids such as hydrochloric acid or citric acid.

The fixing polymers can be used in solubilized form or in the form of dispersions of solid polymer particles.

The cationic fixing polymers which can be used according to the present invention are preferably selected from polymers containing primary, secondary, tertiary and/or quatemary amine groups forming part of the polymer chain or attached directly thereto, and having a molecular weight preferably ranging from about 500 to about 5,000,000 and more preferably from 1000 to 3,000,000.

The anionic fixing polymers generally used are polymers containing groups derived from carboxylic, sulphonic or phosphoric acid and preferably have a weight-average molecular weight ranging from approximately 500 to approximately 5,000,000. Such polymers are described in particular in patents and patent applications DE 2,330,956, FR 1,222,944, FR 1,564,110, FR 1,580,545, FR 2,198,719, FR 2,265,782, FR 2,265,781, FR 2,350,384, FR 2,357,241, FR 2,439,798, GB 839,805, LU 75370, LU 75371, U.S. Pat. No. 2,047,398, U.S. Pat. No. 2,723,248, U.S. Pat. No. 2,102,113, and U.S. Pat. No. 4,128,631, the disclosures of which are specifically incorporated by reference herein. They are chosen in particular from the products sold under the names VERSICOL® E or K by the company Allied Colloid, AMERHOLD® DR 25 by the company Amerchol, QUADRAMER® by the company American Cyanamid, ARISTOFLEX®A, LUVIFLEX® VBM 70, LUVIMER® 100 P or MAEX or MAE, ULTRAHOLD® and ULTRAHOLD® STRONG by the company BASF, COSMEDIA® POLYMER HSP 1180 by the company Henkel, RETEN® 421, 423 or 425 by the company Hercules; ACRYLIDONE® LM, GANTREZ® AN or ES and AVANTAGE® CP by the company ISP, FLEXAN® 500, FLEXAN® 130 and RESINS 28-29-30, 26-13-14 or 28-13-10 by the company National Starch, ACUDYNE® 255 by the company Rohm & Haas, EUDRAGIT® L by the company Rohm Pharma and STEPANHOLD® EXTRA by the company Stepan, or the crotonic acid/vinyl acetate/vinyl t-butylbenzoate copolymer from the company Chimex.

The amphoteric fixing polymers which can be used in accordance with the invention are described in particular in French patent FR 1,400,366 and U.S. Pat. No. 3,836,537, the disclosures of which are specifically incorporated by reference herein. They are selected in particular from the products known by the CTFA (4th Edition, 1991) name octylacrylamide/-acrylates/butylaminoethyl methacrylate copolymer and those sold under the names AMPHOMER®, AMHOMER® LV 71 or LOVOCRYL® 47 by the company National Starch, DIAFORMER® Z301 by the company Sandoz and EVALSAN® by the company Jan Dekker.

The conditioning materials which are useful according to the invention include the usual cosmetic conditioning materials. They are selected in particular from cationic surfactants, anionic or nonionic or cationic or amphoteric polymers, proteins, protein hydrolysates, ceramides, pseudoceramides, fatty acids with linear or branched $C_{16}$–$C_{40}$ chains, such as 18-methyl eicosanoic acid, volatile or non-volatile silicones, which may or may not be soluble in the medium, and mixtures thereof.

The conditioners of cationic polymer type which are useful according to the invention can be chosen from all of those already known per se as improving the cosmetic qualities of the hair, namely, in particular, those described in patent applications EP 0,337,354, FR 2,270,846, FR 2,383, 660, FR 2,598,611, FR 2,470,596, and FR 2,519,863, the disclosures of which are specifically incorporated by reference herein. Among all of the cationic polymers which can be used in the context of the present invention, it is preferred to use quatemary cellulose ether derivatives such as the products sold under the name JR 400® by the company Union Carbide Corporation, cyclopolymers, in particular homopolymers of diallyidimethylammonium salt and copolymers of diallyidimethylammonium salt and of acrylamide, in particular the chlorides, sold under the names MERQUAT® 100, MERQUAT® 550 and MERQUAT® S by the company Merck, cationic polysaccharides and more particularly guar gums modified with 2,3-epoxypropyl- trimethylammonium chloride, sold for example under the name JAGUAR C13S® by the company Meyhall.

Among the sheen reinforcers mention may be made of non-volatile arylsilicones, in particular polyalkylarylsiloxanes such as the phenylsilicone sold under the name DC 556 by the company Dow Corning and diphenyidimethicone sold under the name MIRASIL® DPDM by the company Rhone-Poulenc.

Among the hair dyes, mention may be made in particular of direct dyes. Among those used conventionally, mention may be made of nitrobenzene dyes such as nitrophenylenediamines, nitrodiphenylamines, nitroanilines, nitrophenol ethers or nitrophenols, nitropyridines, anthraquinone dyes, mono- or diazo dyes, triarylmethane dyes, azine dyes, acridine dyes and xanthene dyes or alternatively metalliferous dyes. These direct dyes, in salified or base form, are generally present in the composition according to the invention in proportions which can preferably range from about 0.001 to about 10%, and more preferably from about 0.05 to about 5%, by weight, relative to the total weight of the composition.

For use as a make-up composition, the composition according to the invention can comprise materials that are common for make-up compositions, in particular fillers and/or dyestuffs.

Preferably, the amount of fillers present in the composition according to the invention ranges from 0.01 to 60% by weight relative to the total weight of the composition, more preferably from 2 to 30% by weight.

The amount of dyestuffs preferably ranges 0.01 to 30% by weight relative to the total weight of the composition, more preferably from 1 to 15% by weight.

The fillers are natural or synthetic materials whose main function is modifying the physicochemical (rheological, mechanical, optical) and/or cosmetic properties of a composition. Among the fillers, mention may be made of talc, mica, silica, kaolin, NYLON® powders (in particular ORGASOL), polyethylene powders, TEFLON®, starch, boron nitride, copolymer microspheres such as EXPANCEL® (Nobel Industries), POLYTRAP® (Dow Corning) and silicone resin microbeads (for example TOSPEARLS® from Toshiba).

The dyestuffs are natural or synthetic materials used to give a material a durable colour. A distinction may be made between dyes, on the one hand, and pigments, on the other hand. Dyes are natural or synthetic substances (or materials) that are essentially soluble in their medium of use, the main function is in giving a colour. Mention may be made of natural organic dyes such as cochineal carmine (CI 75 470), or synthetic organic dyes such as haloacid, azo or anthraquinone dyes. Mention may also be made of inorganic dyes such as copper sulphate. Pigments are natural or synthetic substances (or materials) consisting of fine particles which, in contrast with dyes, are insoluble in their medium of use, the main function of which is in giving a colour. Different types of pigments are distinguished; inorganic pigments, organic pigments, lakes or pearlescent pigments.

Lakes are dyes adsorbed onto insoluble particles, the assembly remaining insoluble in its medium of use. Pearlescent pigments are natural or synthetic substances (or materials) which diffract and reflect light to give an iridescent or shiny effect.

Among the inorganic pigments, mention may be made of metal oxides, in particular zirconium oxide, cerium oxide, zinc oxide or chromium oxide (CI 77288), titanium dioxide (CI 77891), black, yellow, red and brown iron oxides (CI 77499, CI 77492, CI 77491), manganese violet (CI 77742), ultramarine blue (CI 77007), ferric blue (CI 77510), chromium hydrate (CI 77289), silver powder or aluminium powder.

Among the organic pigments, mention may be made of carbon black (CI 77266) or D & C Red 36. The lakes generally consist of metal (Al, Zr, Ca, Na) salts of organic dyes, adsorbed onto alumina particles. Mention may be made of those known under the names: D & C Red 21 (CI 45 380), D & C Orange 5 (CI 45370), D & C Red 27 (CI 45 410), D & C Orange 10 (CI 45 425), D & C Red 3 (CI 45 430), D & C Red 7 (CI 15 850:1), D & C Red 4 (CI 15 510), D & C Red 33 (CI 17 200), D & C Yellow 5 (CI 19 140), D & C Yellow 6 (CI 15 985), D & C Green 5 (CI 61 570), D & C Yellow 10 (CI 77 002), D & C Green 3 (CI 42 053), D & C Blue 1 (CI 42 090).

Among the pearlescent pigments, mention may be made of mica coated with titanium oxide, with bismuth oxychloride, with iron oxide or with natural pigments, for example colored titanium mica.

When the composition is a care composition, it preferably comprises active agents such as ascorbic acid, kojic acid, citric acid, caffeic acid, salicylic acid and its derivatives (for example 5-n-octanoylsalicylic or 5-decanoylsalicylic acid), α-hydroxy acids, retinoic acid and its derivatives such as retinol and retinol esters, benzene-1,4-di(3-methylidene-10-camphorsulphonic acid). Any natural or synthetic compound containing such acids, such as plant extracts and more especially fruit extracts, or alternatively xanthine derivatives (caffeine, theophylline), β-glycyrrhetinic acid or asiatic acid, can also be used. Moisturizers such as polyols, in particular glycerol, or surfactants such as proteins of plant origin can also be used.

Depending on the use envisaged and on the physicochemical and/or cosmetic properties of the composition according to the invention, it can also comprise additional gelling agents so as to modify its properties of softness or of hardness, and it can additionally comprise latices or pseudolatices which increase the remanence to water of the composition and give it sheen, or alternatively one or more silicone gums which give the final compositions qualities of softness and slipperiness.

Among the gelling agents which can be used in the composition according to the invention, mention may be made of algal extracts such as agar-agar, carrageenans, alginates; seed extracts such as carob gum, guar gum; plant exudates such as gum arabic, karaya gum, gum tragacanth, ghatti gum; microorganism exudates such as xanthan gum, cellulose or its derivatives such as carboxymethylcellulose, hydroxypropylcellulose, methylcellulose, hydroxypropylmethylcellulose or hydroxyethylcellulose and celluloses modified in particular by grafting an alkyl group; fruit extracts such as pectins; gelling agents of animal origin such as gelatin, caseinates; water-soluble gelling synthetic polymers such as crosslinked polyacrylic acids such as "CARBOPOL" or "PEMULEN" sold by the company Goodrich; silicon derivatives such as synthetic hectorites, for instance the products "LAPONITE RD and RDS" sold by the company Waverly, aluminium magnesium silicates, for instance the product "VEEGUM" sold by the company Vanderbilt. It is understood that these additional gelling agents added to the solid composition according to the invention will not modify the rheological properties of the solid matrix constituting it.

A person skilled in the art will know how to determine the process for preparing the composition according to the invention as a function of its constituents. Since the solid matrix constituting it has a viscosity which decreases greatly under a strain greater than or equal to the shear strain $C_1$, it is possible to mix the various components of the composition together at an appropriate temperature, and then, once the desired homogeneity has been obtained, to give the composition a shape according to a usual method, in particular by leaving it to stand in a mould corresponding to the shape.

The present invention also relates to the cosmetic use of a composition as defined above.

Lastly, the invention relates to a cosmetic treatment process for the skin, mucous membranes, the hair or the exoskeleton, in which the composition as defined above is applied to the skin, mucous membranes, the hair or the exoskeleton.

The examples below allow the present invention to be illustrated without, however, seeking to limit its scope. The percentages are expressed on a weight basis relative to the total weight of the composition. The percentages of ethylene glycol isophthalate/terephthalate/sulphoisophthalate copolymer in the compositions are percentages of active material. For Examples 1 and 2, the viscosities were measured at 25° C. with a control stress rheometer (HAAKERS 150) having a cone-plate measurement device with a one (1) degree angle and a diameter ($\phi$)# of 3.5 cm.

EXAMPLE 1

Preparation of a Terephthalic Copolyester Oligomer

The following reactants were introduced into a 7.5-liter stainless-steel reactor fitted with an anchor-shaped stirrer rotating at 80 rev/min, connected to a Kyowa torsion meter, a jacket for circulating a heat-exchange liquid, and a distillation column controlled by an electrovalve:

11.47 mol of dimethyl terephthalate 2.53 mol of sodium dimethyl isophthalate-5 sulphonate 39.16 mol of ethylene glycol 54 ppm by weight of titanium, in the form of titanium aminotriethanolate as catalyst and etherification-limiting agent.

The mixture was preheated to 180° C. It was then brought to a temperature of 220° C. over about 130 minutes, in order to distill off more than 90% of the theoretical amount of methanol.

The reaction mixture was then brought to 230° C. over 30 minutes. When the reaction mass reached this temperature, a suspension having the composition below was introduced over 60 minutes, still at 230° C.:

0.5 mol of isophthalic acid 2.36 mol of terephthalic acid 8 mol of ethylene glycol.

The reaction mass was then brought to a temperature of 250° C. over 60 minutes.

During the period of introduction of the mixture and during the period of heating up to 250° C., a mixture of water and ethylene glycol was distilled off without retrogradation.

The reaction mixture was then transferred into an autoclave preheated to 250° C. and was then placed under a reduced pressure of 100 millibar over 22 minutes. After 2 minutes under these temperature and pressure conditions, the reaction mass was cast and cooled.

The copolyester obtained had the structural characteristics described in Table 1 below, in which:

"mol % of diacid units" corresponds to the content, in %, of each diacid or diester used relative to the total amount of diacids or diesters used.

"Tp" means: terephthalic unit

"Ip" means: isophthalic unit

"SIp" means: sulphoisophthalic unit

The characteristics of the "glycol" part of the copolyesters were obtained by methanolysis of the products at 190° C. for 16 hours, followed by analysis by the gas chromatography technique and assaying by internal calibration.

"mol % of diol units" corresponds to the content, in %, of oxyethylene units "G", di(oxyethylene) units "2G", tri(oxyethylene) units "3G" and tetra(oxyethylene) units "4G", relative to the total amount of diol units.

"%GT/Σ units" corresponds to the mol % of units of formula (I)

$$[-CO-A-CO-O-(CH_2-CH_2-O)_n-] \quad (I)$$

in which

A is 1,4-phenylene and n=1 relative to the total amount of units of formula (I) wherein A is 1,4-phenylene, sulpho-1,3-phenylene and optionally 1,3-phenylene and n ranges from 1 to 4

"%GT/Σ units" is calculated by the following formula:

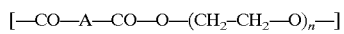

%GT/Σ units=(mol % of Tp units)×(mol % of G units)/100

The molar mass of the polyesters (Mw) is determined by gel permeation chromatography (GPC) in 100% DMAc/LiBr, the results being given in polystyrene equivalents.

| mol % of diacid units | |
|---|---|
| Tp | 82 |
| Ip | 3 |
| SIp | 15 |
| % GT/Σ units | 46.5 |
| mol % of diol units | |
| G | 56.8 |
| 2G | 30.7 |
| 3G | 10 |
| 4G | 2.5 |
| Mw | 8000 |

EXAMPLE 2

Styling Stick

An aqueously gel was prepared by mixing together, under cold conditions, 20% of oligomer of Example 1 and the remainder to 100% of demineralized water. The fluid gel obtained was poured into a mould and left to stand for 24 hours. After setting to a solid, a styling stick was obtained having the following rheological properties:

Initial viscosity $V_0$: =90,000 Pa·s

Shear strain $C_1$: =500 Pa

Viscosity $V_2$ at a strain of 1500 Pa: 30 Pa·s

EXAMPLE 3

Styling Stick

The procedure of Example 2 was repeated with 25% of oligomer of Example 1 and 3% of polyvinylpyrrolidone/vinyl acetate copolymer. A styling stick having rheological properties comparable to those of the product of Example 2 was obtained.

EXAMPLE 4

Sheen Stick

The procedure of Example 2 was repeated with 25% of oligomer of Example 1 and 10% of oil 70641 /V200 from the company Rhône-Poulenc. A sheen stick having rheological properties comparable to those of the product of Example 2 was obtained.

EXAMPLE 5

Deodorant Stick

The procedure of Example 2 was repeated with 20% of oligomer of Example 1 and 0.25% of triclosan. A deodorant stick having rheological properties comparable to those of the product of Example 2 was obtained.

EXAMPLE 6

Lipstick

The procedure of Example 2 was repeated with 20% of oligomer of Example 1, 5% of pigments and 1% of preserving agent. An aqueous lipstick having rheological properties comparable to those of the product of Example 2 was obtained. The stick applied easily to the lips, gave a sensation of freshness when applied and formed a shiny, transfer-free film.

We claim:

1. An aqueous solid topical composition comprising an aqueous solid matrix having the appearance of a gel and possessing the following rheological profile:

an initial viscosity at rest $V_0$ which is sufficient to form a solid composition, wherein said viscosity $V_0$ is stable up to a shear strain $C_1$, a viscosity $V_2$ after shear at a strain $C_2$ for which the ratio $V_0/V_2$ is greater than or equal to 1000:1, the difference $C_2-C_1$ being less than or equal to 1000 Pa, wherein said aqueous solid matrix comprises at least one hydrophilic gelling polymer, wherein said at least one hydrophilic gelling polymer is a water-soluble or water-dispersible terephthalic copolyester oligomer comprising repeating dicarboxylate units of formula (I):

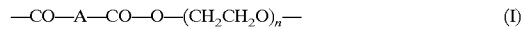

$$-CO-A-CO-O-(CH_2CH_2O)_n- \quad (I)$$

in which

A represents a 1,4-phenylene, sulpho-1,3-phenylene or 1,3-phenylene group, n ranges from 1 to 4, and wherein in at least 35 mol % of said units of formula (I), A represents a 1,4-phenylene group and n is equal to 1, in at least 7 mol % of said units of formula (I), A represents a sulpho-1,3-phenylene group, and optionally in up to 20 mol % of said units of formula (I), A represents a 1,3-phenylene group,
wherein the weight-average molecular mass of said copolyester oligomer is less than 20,000.

2. An aqueous solid topical composition according to claim 1, wherein said initial viscosity $V_0$ ranges from 50,000 to 1,000,000 Pa·s.

3. An aqueous solid topical composition according to claim 1, wherein said aqueous solid matrix has a viscosity $V_1$ at the-starting shear strain $C_1$, and wherein the ratio $V_0/V_1$ is less than or equal to 2.

4. An aqueous solid topical composition according to claim 1, wherein said shear strain $C_1$ is at least 500 Pa.

5. An aqueous solid topical composition according to claim 1, wherein the change in viscosity induced by shear is not immediately reversible.

6. An aqueous solid topical composition according to claim 1, wherein said units of formula (I) for which A represents a 1,4-phenylene group and n is equal to 1 are present in an amount of at least 40 mol %.

7. An aqueous solid topical composition according to claim 6, wherein said units of formula (I) for which A represents a 1,4-phenylene group and n is equal to 1 are present in an amount ranging from 40 to 90 mol %.

8. An aqueous solid topical composition according to claim 1, wherein said units of formula (I) for which A represents a sulpho-1,3-phenylene group are present in an amount of at least 10 mol %.

9. An aqueous solid topical composition according to claim 8, wherein said units of formula (I) for which A represents a sulpho-1,3-phenylene group are present in an amount of ranging from 10 mol % to 25 mol %.

10. An aqueous solid topical composition according to claim 1, wherein said units of formula (I) for which A represents a 1,3-phenylene group are present in an amount up to 20 mol %.

11. An aqueous solid topical composition according to claim 10, wherein said units of formula (I) for which A represents a 1,3-phenylene group are present in an amount up to 5 mol %.

12. An aqueous solid topical composition according to claim 1, wherein said weight-average molecular mass of said copolyester oligomer is less than 15,000.

13. An aqueous solid topical composition according to claim 12, wherein said weight-average molecular mass of said copolyester oligomer ranges from 5000 to 14,000.

14. An aqueous solid topical composition according to claim 13, wherein said weight-average molecular mass of said copolyester oligomer ranges from 8000 to 10,000.

15. An aqueous solid topical composition according to claim 1, wherein said hydrophilic gelling, polymer is present in an amount ranging from 10 to 40% by weight relative to the total weight of said composition.

16. An aqueous solid topical composition according to claim 15, wherein said hydrophilic gelling polymer is present in an amount ranging from 10 to 30% by weight relative to the total weight of said composition.

17. An aqueous solid topical composition according to claim 1, wherein said composition is in a form to be applied to the skin, mucous membranes or the exoskeleton.

18. An aqueous solid topical composition according to claim 1 wherein said composition further comprises a fatty phase.

19. An aqueous solid topical composition according to claim 1, wherein said composition further comprises at least one additive and/or active agent common in dermatocosmetics.

20. An aqueous solid topical composition according to claim 19, wherein said at least one additive and/or active agent is selected from: fragrances; stabilizing agents; UV-A and UV-B sunscreening agents; hydrophilic and lipophilic antioxidants; chelating agents; $\alpha$- and $\beta$-hydroxyacids, ceramides, antidandruff agents, antiacne agents, agents for combating hair loss; antifungal and antiseptic agents; active substances of antiperspirant type and bacterial type and odor absorbers; hair fixing material and conditioning material; hair care active agents and skin-reinforcing agents and hair dyes; fillers; dyestuff, gelling material; and silicone gums.

21. An aqueous solid topical composition according to claim 17, wherein said composition is in the form of a body hygiene composition, a hair composition, a make-up composition or a care composition.

22. An aqueous solid topical composition according to claim 21, wherein said make-up composition is a lip composition.

23. An aqueous solid topical composition according to claim 21, wherein said make-up composition is a transfer-free make-up composition.

24. A process for cosmetically treating human skin, a mucous membrane, hair, or exoskeleton, in which an effective amount of at least one composition according to claim 10 is applied to said skin, mucous membrane, hair, or exoskeleton.

* * * * *

UNITED STATES PATENT AND TRADEMARK OFFICE
CERTIFICATE OF CORRECTION

PATENT NO. : 6,338,858 B1 Page 1 of 1
DATED : January 15, 2002
INVENTOR(S) : Christine Dupius, Henri Samain, Véronique Roulier and Véronique Ferrari It is certified that error appears in the above-identified patent and that said Letters Patent is hereby corrected as shown below:

<u>Column 13,</u>
Line 10, "the-starting" should read -- the starting --.

<u>Column 14,</u>
Line 2, "gelling, polymer" should read -- gelling polymer --.
Line 13, "claim 1 wherein" should read -- claim 1, wherein --.
Lines 45 and 46, "claim 10" should read -- claim 1 --.

Signed and Sealed this

Twenty-seventh Day of August, 2002

Attest:

Attesting Officer

JAMES E. ROGAN
Director of the United States Patent and Trademark Office